United States Patent [19]

Klaubert

[11] 4,262,125
[45] Apr. 14, 1981

[54] (1H-IMIDAZOL-5-YLMETHYL)ISOTHIOUREAS

[75] Inventor: Dieter H. Klaubert, Perkiomenville, Pa.

[73] Assignee: American Home Products Corporation, New York, N.Y.

[21] Appl. No.: 59,808

[22] Filed: Jul. 23, 1979

[51] Int. Cl.³ .................. C07D 401/12; C07D 233/64
[52] U.S. Cl. .................. 546/278; 424/263; 424/273 R; 548/336; 260/245.6
[58] Field of Search .................. 546/278; 548/336; 260/245.6

[56] References Cited

U.S. PATENT DOCUMENTS

| 3,759,944 | 9/1973 | Black et al. | 548/336 X |
| 4,036,971 | 7/1977 | Durant et al. | 546/278 |

FOREIGN PATENT DOCUMENTS 1296544  11/1972  United Kingdom .................. 546/278

OTHER PUBLICATIONS

Turner, Chemical Abstracts vol. 43, col. 634 (1949).
Black et al., Chem. Abstracts, vol. 86, abst. No. 145927t (1977).
Black et al., Chem. Abstracts, vol. 85, abst. 104,199t (1976).
Black et al., Chem. Abstracts vol. 75, abst. 118,317k (1971).
Black et al., Chem. Abstracts vol. 75, abst. 20399p (1971). prior cited.
Turner, J. Am. Chem. Soc. vol. 70, p. 3523 (1948).

Primary Examiner—John D. Randolph
Attorney, Agent, or Firm—Richard K. Jackson

[57] ABSTRACT

Anti-secretory, anti-hypertensive agents of the formula are presented:

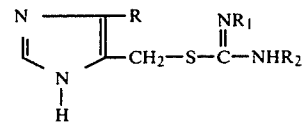

in which
R is alkyl of 1 to 6 carbon atoms;
$R_1$ is hydrogen or alkyl of 1 to 6 carbon atoms;
$R_2$ is hydrogen, alkyl of 1 to 6 carbon atoms; phenyl,

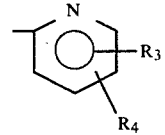

wherein $R_3$ and $R_4$ are independently hydrogen, alkyl of 1 to 6 carbon atoms alkoxy of 1 to 6 carbon atoms, or —CH₃, or $R_2$ and $R_1$ taken together are ethylene or tetramethylene;

or a pharmaceutically acceptable acid addition salt thereof.

6 Claims, No Drawings

(1H-IMIDAZOL-5-YLMETHYL)ISOTHIOUREAS

BRIEF DESCRIPTION OF THE INVENTION

Certain derivatives of (1H-imidazol-5-ylmethyl)isothioureas of the general formula:

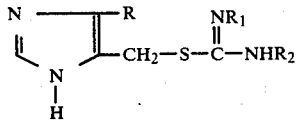

are valuable gastric anti-secretory agents useful for treatment of peptic ulcer disease and anti-hypertensive agents useful for treatment of hypertension.

DETAILED DESCRIPTION OF THE INVENTION

In accordance with this invention there is provided a novel group of anti-secretory anti-hypertensive agents of the formula:

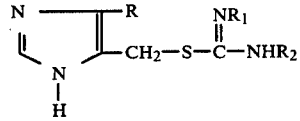

in which

R is alkyl of 1 to 6 carbon atoms; $R_1$ is hydrogen or alkyl of 1 to 6 carbon atoms; $R_2$ is hydrogen, alkyl of 1 to 6 carbon atoms; phenyl,

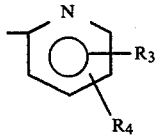

wherein $R_3$ and $R_4$ are independently hydrogen, alkyl of 1 to 6 carbon atoms alkoxy of 1 to 6 carbon atoms or —$CF_3$, or $R_2$ and $R_1$ taken together are ethylene or tetramethylene;

or a pharmaceutically acceptable acid addition salt thereof.

It is to be understood that the compounds structurally depicted throughout this specification and in the appended claims exist as 1H-4(5)imidazolyl tautomers of methyl-isothioureas

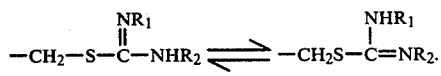

It is applicant's intention to embrace all of the tautomers by depiction of one tautomeric form throughout this application.

Within the scope of the compound genus depicted supra are the preferred anti-hypertensive agents comprising those compounds in which $R_2$ is

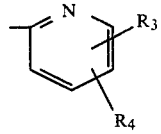

and more preferably those compounds in which the alkyl and/or alkoxy substituents present in the molecule contain from 1 to 3 carbon atoms. These preferred N-(2-pyridinyl)carbamimidothioic acid (1H-imidazolylmethyl)ester derivatives excell as long term anti-hypertensive agents.

The compounds of this invention are produced by reaction of an appropriately substituted 4(5)-halomethyl-imidazole hydrohalide with thiourea or an appropriately substituted thiourea, where "halo" and "halide" refer to chlorine or bromine. The product hydrochloride or hydrobromide salts are converted to the free base, if desired, by methods known in the art. Likewise, conversion of one salt to another may be conventionally accomplished by conversion to the free base followed by neutralization with the desired acid or by treatment of a given salt with an ion-exchange resin on the desired cycle.

The gastric anti-secretory activity of the compounds of this invention was established with the following scientifically recognized, standard test for anti-secretory activity:

Male Charles River rats of Sprague-Dawley strain and 190 to 240 gm. body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was adminisitered intraduodenally. The rats are sacrificed by $CO_2$ asphyxiation four hours after pyloric ligation. The stomachs are removed and the gatric contents emptied into graduated centrifuge tubes. The gastric samples are centrifuged for 20 minutes and those obviously contaminated by food, blood or feces are discarded. The volume of gastric fluid is recorded and the acid concentration of 1.0 ml. sample aliquots is measured by electrometric titration to pH 7.0 with 0.1 N NaOH. The calculated product of gastric volume (ml/4 hr) and acid concentration (mEq/L) estimates the total acid output (TAO, mEq/4 hr) over the four-hour test period. An analysis of variance is performed on these data to determine statistically significant ($p<0.05$) deviation between control versus drug-treated groups.

The dosage regimen for therapeutic use of the anti-secretory agents disclosed herein will vary with the mode of administration, size and age of the person under treatment as well as the severity of the dysfunction. Therefore, treatment of peptic ulcer disease must be individualized for the patient under the guidance of the attending physician.

The anti-hypertensive activity of the compounds of this invention was established with the following scientifically recognized, standard test in which the systolic pressure of male spontaneously hypertensive rats is indirectly measured with a sensor such as the Decker Caudal Plethysmorgraph. The blood pressure readings are made prior to oral administration of the compound being tested and 1.5, 4 and 24 hours after administration. Each of the compounds exemplified in this specification demonstrated a decrease in blood pressure at a dose from about 10 to about 75 milligrams per kilogram for periods of 1.5 and 4 hours, while the 2-pyridinyl derivative of Example IV demonstrated a marked decrease in blood pressure for the full 24 hour period at a dose of 25 milligrams per kilogram and a marked decrease in blood pressure at 10 milligrams per kilogram for 4 hours with no tachycardia.

For treatment of hypertension, the compounds of this invention must be administered under the guidance of a physician. Unit dosage forms containing from about 0.5 to 2 grams for single or plural daily administrations are considered appropriate for oral administration.

The compounds of this invention may be administered by conventional oral or parenteral routes as solids, liquids or isotonic solutions. Conventional adjuvants known to the art may be combined with the compounds disclosed herein to provide compositions and solutions for administration purposes although it is considered desirable and feasible to use the compounds neat or pure without additives other than for the purpose of providing suitable pharmaceutically acceptable solid or liquid dosage unit forms.

The following examples illustrate the preparation of the anti-secretory, anti-hypertensive agents of this invention. An index of gastric anti-secretory activity is reported at the end of each example illustrating the production of a compound disclosed herein. The activity is expressed as percentage inhibition of acid secretion in drug treated animals in comparison to control animals based upon intraduodenal (i.d.) administration of 25 mg/kg of the tested compound, unless indicated otherwise.

EXAMPLE 1

Carbamimidothioic acid (4-methyl-1H-imidazol-5-ylmethyl)ester, dihydrobromide

A mixture of 12.8 g of 4-bromomethyl-5-methyl imidazole hydrobromide and 4 g. of thiourea in 200 ml. of EtOH is heated at reflux for 3 hr., cooled and the product is filtered off to give the title compound, m.p. 130°-132° C. (dec.).

Calculated for: $C_6H_{10}N_4S \cdot 2HBr$: C, 21.69; H, 3.64; N, 16.86;
Found: C, 21.54; H, 3.53; N, 16.81.
Percentage inhibition: 87

EXAMPLE 2

4,5-dihydro-2-[(4-methyl-1H-imidazol-5-ylmethyl)-thio]-1H-imidazole, dihydrobromide This product is prepared in a manner identical to Example 1 using 2-imidazolinethione instead of thiourea. The product is separated by filtration, m.p. 280°-282° C. (dec).

Calculated for: $C_8H_{12}N_4S \cdot 2HBr$: C, 26.83; H, 3.94; N, 15.65;
Found: C, 26,68; H, 3.97; N, 15.63.
Percentage Inhibition: 88

EXAMPLE 3

Phenylcarbamimidothioic acid (4-methyl-1H-imidazol-5-ylmethyl) ester, dihydrobromide Using 1-phenylthiourea instead of thiourea and t-butanol as a solvent in a manner similar to Example 1 the desired product is isolated, m.p. 198°-202° C. (dec.).

Calculated for: $C_{12}H_{14}N_4S \cdot 2HBr$: C, 35.31; H, 3.95; N, 13,73
Found: C, 34.93; H, 3.87; N, 13.47
Percentage Inhibition: 97

EXAMPLE 4

N-(2-pyridinyl)carbamimidothioic acid (4-methyl-1H-imidazol-5-ylmethyl) ester, dihydrobromide, ethanolate The title compound is prepared as in Example 3 using 1-(2-pyridine)-thiourea. The product is crystallized from EtOH-Et$_2$O, m.p. 115°–117° C.

Calculated for: $C_{11}H_{13}N_5S \cdot 2HBr \cdot EtOH$: C, 34.30; H, 4.64; N, 15.39;
Found: C, 34.07; H, 4,81; N, 15.36.
Percentage Inhibition: 98

EXAMPLE 5

4,5,6,7-tetrahydro-2-[(5-methyl-1H-imidazol-4-yl)methylthio]-1H1,3-diazepine, dihydrobromide Following the procedure of Example 1, with the exception that 1,3-diazepine-2-thial instead of thiourea—the title compound is obtained, m.p. 209°–211° C. (dec.).

Calculated for: $C_{10}H_{18}N_4Br_2S$: C, 31.10; H, 4,70; N, 14.51; S, 8.30;
Found: C, 31.12; H, 4.95; N, 14.64; S, 8.40.
Percentage Inhibition: 74

What is claimed is:

1. A compound of the formula:

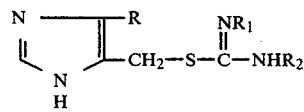

in which
R is alkyl of 1 to 6 carbon atoms;
$R^1$ is hydrogen or alkyl of 1 to 6 carbon atoms;
$R_2$ is

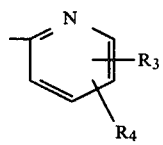

wherein $R_3$ and $R_4$ are independently hydrogen, alkyl of 1 to 6 carbon atoms, alkoxy of 1 to 6 carbon atoms, or —$CF_3$, or $R_1$ and $R_2$ taken together are ethylene or tetramethylene;
or a pharmaceutically acceptable acid addition salt thereof.

2. A compound of claim 1 of the formula:

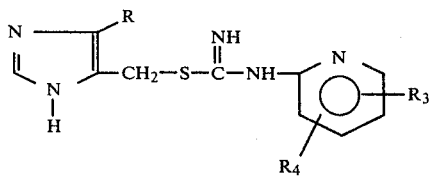

in which
R is alkyl of 1 to 6 carbon atoms; and $R_3$ and $R_4$ are independently hydrogen, alkyl of 1 to 6 carbon atoms, alkoxy of 1 to 6 carbon atoms or $CF_3$;

or a pharmaceutically acceptable acid addition salt thereof.

3. A compound of claim 2 of the formula:

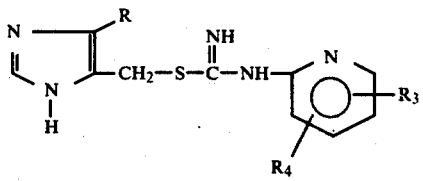

in which

R is alkyl of 1 to 3 carbon atoms;

$R_3$ is hydrogen, alkyl of 1 to 3 carbon atoms, alkoxy of 1 to 3 carbon atoms or —$CF_3$; and $R_4$ is hydrogen or alkyl of 1 to 3 carbon atoms or a pharmaceutically acceptable acid addition salt thereof.

4. The compound of claim 1 which is 4,5-dihydro-2-[(4-methyl1H-imidazol-5-ylmethyl)thio]-1H-imidazole or a pharmaceutically acceptable acid addition salt thereof.

5. The compound of claim 3 which is N-(2-pyridinyl)-carbamimidothioic acid (4-methyl-1H-imidazol-5-ylmethyl)ester or a pharmaceutically acceptable acid addition salt thereof.

6. The compound of claim 1 which is 4,5,6,7-tetrahydro-2-(5-methyl-1H-imidazol-4-yl)methylthio-1H-1,3-diazepine or a pharmaceutically acceptable acid addition salt thereof.

* * * * *